(12) United States Patent
Hommann et al.

(10) Patent No.: US 6,974,446 B2
(45) Date of Patent: Dec. 13, 2005

(54) STORAGE CONTAINER COMPRISING A DOSING MEANS FOR DISPENSING AN INJECTABLE PRODUCT TO AN INJECTION DEVICE IN DOSES

(75) Inventors: Edgar Hommann, Grossaffoltern (CH); Ian Thompson, Burgdorf (CH)

(73) Assignee: TecPharma Licensing AG, Burgdorf (CH)

( * ) Notice: Subject to any disclaimer, the term of this patent is extended or adjusted under 35 U.S.C. 154(b) by 128 days.

(21) Appl. No.: 10/341,315

(22) Filed: Jan. 13, 2003

(65) Prior Publication Data
US 2003/0139707 A1    Jul. 24, 2003

Related U.S. Application Data

(63) Continuation of application No. PCT/CH01/00406, filed on Jun. 29, 2001.

(30) Foreign Application Priority Data

Jul. 14, 2000  (DE) ............................. 100 34 270

(51) Int. Cl.⁷ .......................... A61B 19/00; A61M 1/06
(52) U.S. Cl. ..................... 604/411; 604/905; 604/403; 604/415; 604/71
(58) Field of Search .............. 604/68, 71, 72, 604/82, 86, 87, 187, 200–202, 205, 207–209, 604/211, 218, 224, 523, 533–535, 403, 407, 604/411, 415, 416, 903, 905; 220/500–502, 220/200, 202, 203.02, 203.08, 203.19, 253, 220/255, 255.1, 265–267; 222/80, 81, 89–91, 222/153.01, 153.05, 153.06, 541.1–541.2, 222/541.6–541.8, 544, 562

(56) References Cited

U.S. PATENT DOCUMENTS

| 4,338,980 | A |   | 7/1982  | Schwebel et al. |
|-----------|---|---|---------|-----------------|
| 4,507,113 | A |   | 3/1985  | Dunlap          |
| 4,662,878 | A | * | 5/1987  | Lindmayer ................... 604/411 |
| 4,913,699 | A |   | 4/1990  | Parsons         |
| 5,062,830 | A | * | 11/1991 | Dunlap ........................ 604/68 |
| 5,649,912 | A |   | 7/1997  | Peterson        |
| 5,704,911 | A |   | 1/1998  | Parsons         |
| 5,846,233 | A | * | 12/1998 | Lilley et al. ................. 604/414 |
| 6,132,395 | A | * | 10/2000 | Landau et al. ................ 604/68 |
| 6,599,264 | B1| * | 7/2003  | Erni et al. .................... 604/68 |

FOREIGN PATENT DOCUMENTS

| DE | 19948988 | 4/2000  |
|----|----------|---------|
| FR | 2762990  | 11/1998 |

* cited by examiner

*Primary Examiner*—Patricia Bianco
(74) *Attorney, Agent, or Firm*—Dorsey & Whitney LLP

(57) ABSTRACT

A combination of a storage container for an injectable product and a needleless injection device for injecting the product, wherein an adapter is used to establish a fluid connection between the storage container and the injection device, wherein the storage container is connected to a dosing means for dispensing the injectable product to the injection device in doses, and the dosing means includes an actuator arranged in the storage container or reaching into the storage container.

18 Claims, 3 Drawing Sheets

STORAGE CONTAINER COMPRISING A DOSING MEANS FOR DISPENSING AN INJECTABLE PRODUCT TO AN INJECTION DEVICE IN DOSES

CROSS-REFERENCE TO RELATED APPLICATIONS

This application is a continuation of International Patent Application No. PCT/CH01/00406, filed on Jun. 29, 2001, which claims priority to German Patent Application No. 100 34 270.1, filed on Jul. 14, 2000, both of which are incorporated herein by reference.

BACKGROUND

The invention relates to a combination of a storage container for an injectable product and a needleless injection device for injecting the product. An adapter is used to establish a fluid connection between the storage container and the injection device. The needleless injection device is in particular a disposable injection pen. The combination is preferably used for a medicine, in particular insulin.

A combination of a storage container for an injectable product and a needleless injection device for injecting the product is known from U.S. Pat. No. 4,913,699. A transfer container comprising a dosing device is placed onto an ampoule in which the injectable product is situated. The dosing device transfers a dosed quantity of the product from the ampoule into the transfer container. The dosed quantity of the product is then passed on to a needleless injection device. The product penetrates into a product space of the injection device through an injection opening, wherein a moving piston is displaced and so enlarges the product space. In order to inject the product, this piston is pushed back towards the injection opening and thus forces the product out through the injection opening. The injection is performed with sufficiently high pressure that the product is injected directly under the skin without an injection needle, if the injection opening is placed on the skin. The piston is preferably moved towards the injection opening by means of gas pressure or spring force.

SUMMARY

It is an object of the present invention to provide a combination of a storage container and a needleless injection device which is easier for a user to handle. In addition, the intention is to enable the combination to be manufactured more cheaply.

The storage container is connected to a dosing means for dispensing the injectable product to the injection device in doses. The dosing means includes an actuator arranged in the storage container or reaching into the storage container. The storage container is equipped with a dosing means. The storage container can additionally include a separate delivery means. Preferably, the dosing means is simultaneously the delivery means. The storage container and the dosing means are preferably combined in the same device. In this way, the functions of storing and dosing the injectable product are combined in one device. Preferably, a transfer container can be omitted.

The dosing means can include a pump which reaches into the storage container via a line, in particular a cannula, and forces product out of the storage container in doses. The dosing means preferably includes a piston as an actuator which is movably mounted in the storage container. By moving the piston towards an outlet of the storage container by a defined distance, a dosed quantity of the product emerges from the outlet of the storage container. The piston can be moved manually or by a motor. A mechanism for operating the piston can be provided outside the storage container. An operating device for the piston is preferably integrated into the storage container.

The storage container can include a large container, e.g., for use in hospitals, or an ampoule. The storage container is preferably a component of a device for administering the product in doses, to which device the adapter for establishing the fluid connection between the storage container and the needleless injection device or an injection needle can optionally be connected. Preferably, the injection needle or adapter is connected to the device by means of a snap lock or a screw lock. Preferably, injection pens are used which enable the product to be injected in doses via an injection needle. Such pens are known from DE 198 21 934.2 and DE 199 25 904.6. If, instead of the injection needle disclosed therein, the adapter is fixed to the injection pen, a fluid connection can be established between the injection pen serving as the storage container and the needleless injection device. In order to fill the needleless injection device with a dosed quantity of the product, the user does not require a separate dosing device. The injection pen thus obtains a new area of application. In accordance with the invention, it is used to fill the needleless injection device with a dosed quantity of the product.

The user can inject himself with a dosed quantity of the product either by means of the injection pen, via a needle, or can fill a needleless injection device with product in doses and administer the product using the needleless injection device.

Instead of the injection device, for example the injection pen, an infusion device can also be used.

The adapter preferably comprises a needle and an opening connected to the injection opening of the needleless injection device. The storage container is sealed by a membrane, in particular a septum, which can be penetrated by the needle. Since the injection device does not itself comprise a needle to establish a fluid connection in the storage container, the adapter is placed onto the injection opening of the needleless injection device, such that the needle of the adapter projects from the injection device. Using this needle, a fluid connection to the product in the storage container can be established. The adapter can be connected to the injection device via a snap lock. The adapter can also simply be pushed onto the injection device. The adapter is preferably screwed onto the injection device.

The adapter is attached to the injection device in such a way that the opening on the adapter and the injection opening of the injection device have a fluid connection. The two openings are preferably connected to each other via a seal. There is thus no loss as the product is transferred from the storage container to the injection device. The seal preferably consists of an elastic plastic which is pressured by the connection between the adapter and the injection device and thus seals the fluid connection off from the environment.

To establish the fluid connection, the needle of the adapter is pushed through the membrane of the storage container. Preferably, the adapter is in addition fixedly connected to the storage container. The adapter can be screwed or plugged onto the storage container. Particularly preferably, the adapter is fixed to the storage container by means of a snap lock. An advantage of the snap connection is that the needle is prevented from turning in the septum, and so there is no rubber abrasion. A fixing mechanism is achieved by means of a snap lock, using a fixing structure comprising snap cams or notches on the adapter and corresponding counter elements formed in opposition on the storage container or on the ampoule. Such a fixing mechanism is known from WO 95/01812. The adapter can be pushed onto the storage container linearly, creating a fixed, in particular positive-lock connection between the adapter and the storage container. At least one elastically movable snap cam is preferably ejected when at least one counter element, in particular a bulge, is pushed over, said snap cam coming to rest in an end position in the shifting direction, behind the bulge. Preferably, the adapter can be linearly removed from the storage container, wherein the at least one snap cam is pulled in the reverse direction over the bulge. If a barb is used as the cam, linearly removing the adapter from the storage container, even with the use of force, is hindered or prevented.

The bulge is preferably provided on the storage container. Particularly preferably, an external thread is used. The at least one snap cam of the adapter comes to rest at a point on the run of the thread. Simply by turning, the adapter can be unscrewed from the storage container, wherein the snap cam is not ejected but moves along the run of the thread. When a thread is used, a connection by means of a barb can also be released by turning.

Preferably, at least two snap cams, particularly preferably four snap cams, are provided. The snap cams are preferably arranged concentrically around the needle of the adapter. Particularly preferably, non-elastic regions arranged concentrically around the needle are provided between the snap cams, which do not impede the adapter being pushed over onto the storage container.

The snap cams or notches can also be formed on the storage container, and correspondingly the counter elements formed in opposition, in particular the thread, can be formed on the adapter.

A corresponding snap connection can also be provided between the adapter and the needleless injection device.

A snap lock as illustrated above can also be advantageously used in a combination of a storage container for an injectable product and a transfer container. The Applicant reserves the right to direct a divisional application to this.

The transfer container absorbs a dosed quantity of the injectable product from the storage container by means of a dosing means and dispenses the dosed quantity of the injectable product to an injection device, to be injected, wherein the transfer container can be connected to the storage container directly or via an adapter. In accordance with the invention, the transfer container or the adapter is fixed to the storage container via a snap lock which can be snapped onto the storage container. A snap lock can be provided between the adapter and the transfer container and/or between the transfer container and the injection device.

As described above, the snap connections can preferably be released by turning.

The transfer container absorbs a pre-dosed quantity of the injectable product and stores said quantity until the dosed quantity of the product is dispensed to the injection device. To this end, the transfer container is preferably equipped with a delivery device. The storage container can be formed by an injection pen.

The dosing means can be attached on or on the storage container or on the transfer container. The dosing means is preferably integrated in the transfer container. This is provided for if the storage container does not itself include a dosing means. Preferably, a dosed quantity of the product is suctioned out of the storage container by means of a piston in the transfer container and dispensed to an injection device by an opposite movement of the piston. In order to enable dosing to be exact, the piston is preferably moved by means of a thread.

BRIEF DESCRIPTION OF THE DRAWINGS

In the accompanying drawings, identical reference numerals indicate identical or functionally identical elements.

DETAILED DESCRIPTION

Figure 1:
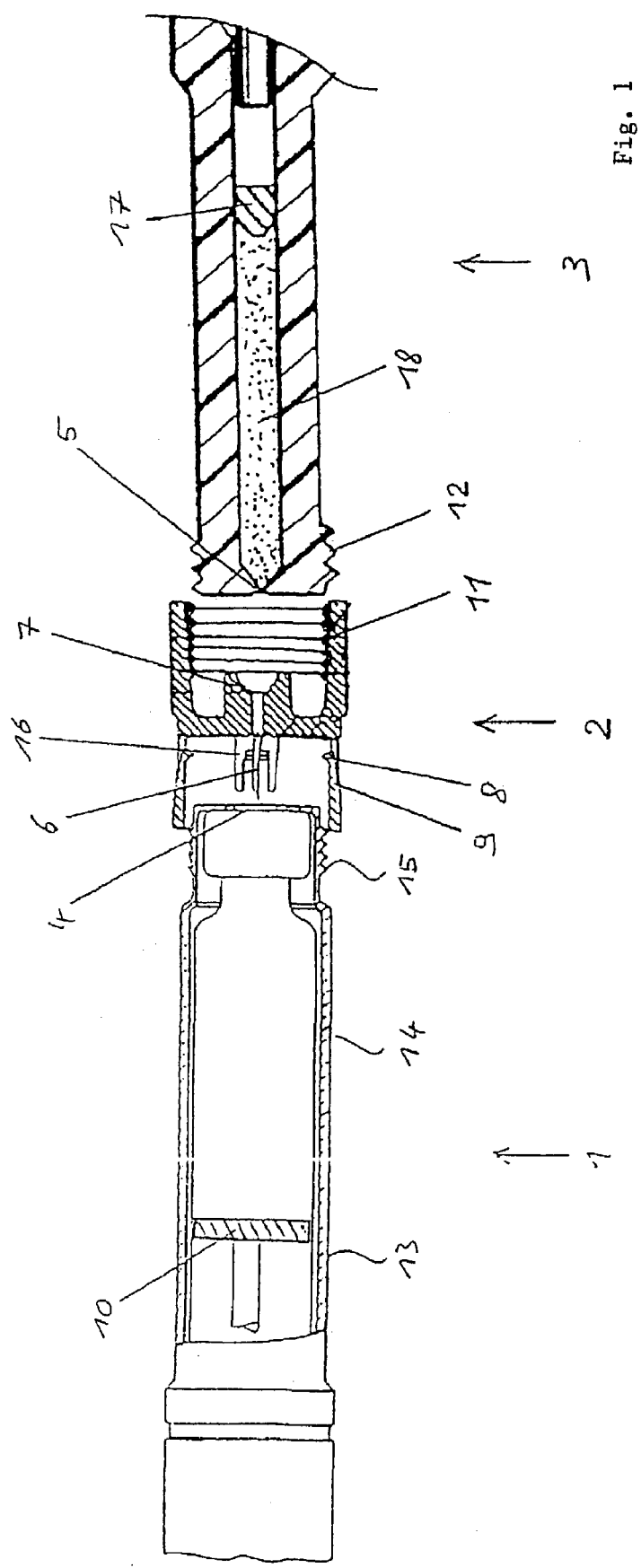
FIG. 1 depicts a storage container comprising an integrated dosing means, in combination with a needleless injection device.

FIG. 1 shows a storage container 1 for an injectable product, an adapter 2 and a needleless injection device 3, before the fluid connection has been established between the storage container 1 and the injection device 3. In order to establish the fluid connection, the adapter 2 is linearly pushed onto the storage container 1 and the injection device 3 is screwed into the adapter 2. The storage container 1 includes a casing 13 in which a substantially cylindrical ampoule 14 is accommodated. A dosing means is integrated in the storage container 1. The dosing means serves to dose and deliver the product. To this end, the piston 10 of the dosing means protrudes into the ampoule 14 through a rear end of the ampoule 14. The ampoule 14 is sealed at its front end by a septum 4. The piston 10 is mounted axially movable in the ampoule 14. It is moved by a dosing mechanism, not shown in the drawing. Any known dosing means can be used. Mechanical dosing, in particular using an adjusting screw, is preferably provided for. The storage container 1 is preferably an injection pen.

The adapter 2 comprises a needle 6 projecting towards the storage container 1. It is surrounded by a sleeve-shaped part of the adapter 2. The needle 6 preferably does not protrude beyond the sleeve-shaped part of the adapter 2 and is thus protected.

A connection can be established between the sleeve-shaped part and the storage container. In the example embodiment, a snap connection is established between the adapter 2 and the storage container 1 using snap cams 8 formed on elastic snap holders 9, by snapping the snap cams 8 on over the front end of the casing 13. Counter elements 15 are correspondingly formed opposite to the snap cams 8 at the front end of the casing 13, via which elements the snap cams 8 of the adapter 2 are pushed, by being pushed over the storage container 1. As the snap cams 8 are pushed over the counter elements 15, the elastic snap holders 9 spring away, radially outwards, with the snap cams 8. After the snap cams 8 have been pushed over them, the snap holders 9 elastically spring back again to their starting position, such that a positive-lock connection is achieved between the adapter 2 and the storage container 1. The counter elements 15 are formed as threads 15 in FIG. 1. The snap cams 8 are arranged axially offset approximately or exactly in accordance with the gradient of the thread 15. As the adapter 2 is pushed onto the storage container 1, the snap cams 8 mesh elastically with the run of the thread 15. The adapter 2 can be unscrewed from the storage container 1 or from the casing 13 by turning, or also by applying force. To this end, the snap cams 8 are formed obliquely in both shifting directions. They can, however, also be formed as barbs, such that linear shifting movement between the adapter 2 and the storage container 1 is only possible in one direction. The other shifting direction is enabled by turning the thread.

Preferably, two or three snap holders 9, particularly preferably four snap holders 9, each comprising a snap cam 8 are arranged at a uniform angular distance from each other, distributed over the circumference of the sleeve-shaped part of the adapter 2. A snap holder 9 consists of a spring-elastic clip formed by removing a U-shaped region 16 in the lateral wall in the sleeve-shaped region of the adapter 2 by which the adapter 2 is pushed via the storage container 1. The adapter 2 is preferably made of an elastic or spring-elastic material. It is preferably made of plastic.

A connection between the adapter 2 and the needleless injection device 3 is established via a second sleeve-shaped region 30. The needle 6 ends in an opening 7 in the interior of said second sleeve-shaped region 30. A seal 31 is arranged concentrically around the opening 7. The second sleeve-shaped region 30 comprises an internal thread 11 with which an external thread 12 of the injection device 3 meshes, to establish a connection. The injection device 3 is screwed via its external thread 12 into the internal thread 11 of the adapter 2, until an injection opening 5 of the injection device 3 obtains a direct fluid connection to the opening 7 of the adapter 2. The fluid connection is sealed off from the environment by a seal. A snap lock 8, 9 can also be used as the connection between the adapter 2 and the injection device 3.

A product space 18 in the injection device 3 is defined by the injection opening 5 and a piston 17 of the injection device which is mounted, linearly shiftable, in the product space 18. When the injection device 3 is unfilled, the piston 17 abuts the injection opening 5. If the injection device 3 is to be filled with a dosed quantity of the injectable product, a fluid connection is established between the storage container 1 and the injection device 3 by means of the adapter 2. From the position shown in FIG. 1, the adapter 2 is linearly pushed onto the front end of the casing 13, wherein the needle 6 pierces the septum 4 of the ampoule 14. The injection device 3 is correspondingly screwed into the adapter 2. Through a linear movement of the piston 17 of the dosing means towards the septum 4, a dosed quantity of the injectable product is displaced through the needle 6, the opening 7 and the injection opening, into the product space 18, wherein the piston 17 is displaced away from the injection opening 5. Once the injection device 3 has been filled, the fluid connection can be interrupted and the dosed product injected in a known way by means of the injection device 3.

Figure 2:
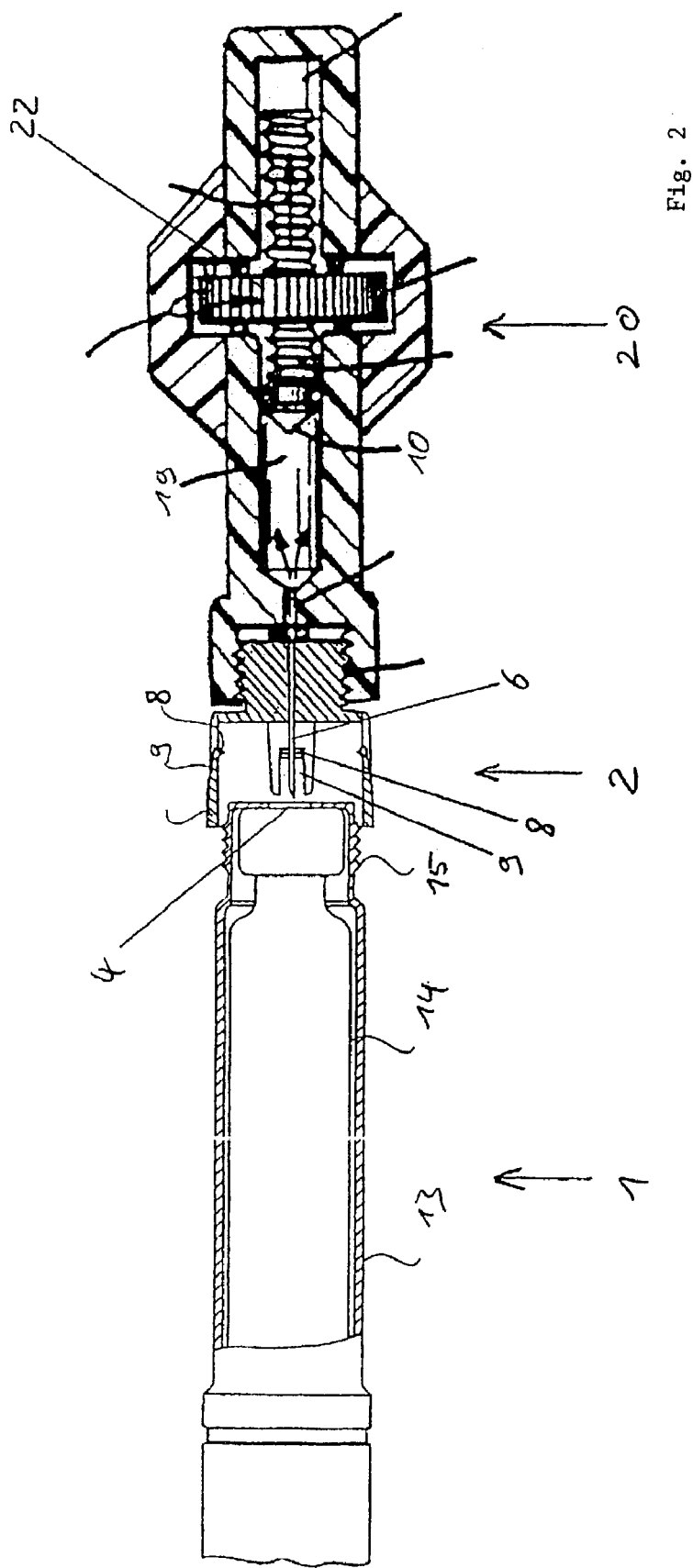
FIG. 2 depicts a storage container in combination with an adapter and a transfer container comprising an integrated dosing means.

FIG. 2 shows a transfer container 20 comprising an integrated dosing means. A fluid connection between the storage container 1 and the transfer container 20 is established via the adapter 2, as described above. The interface of the adapter 2 to the transfer container 20 is formed like the external thread 12 of the injection device 3 from FIG. 1. FIG. 2 shows a fluid connection between the transfer container 20 and the adapter 2. There is no fluid connection between the adapter 2 and the storage container 1. In order to establish the fluid connection, the adapter 2 is pushed onto the storage container 1 via its snap lock 8, 9.

If a fluid connection has been established, a dosed quantity of the product can be suctioned from the ampoule 14 into a transfer space 19 by means of the dosing means 10, 22. To this end, a piston 10 is moved linearly backwards and so enlarges the transfer space 19, such that product flows after it out of the ampoule 14. If the desired quantity of the product is situated in the transfer container 20, the transfer container 20 is detached from the adapter 2 and screwed onto the needleless injection device 3. The transfer space 19 is reduced by shifting the piston in the reverse direction, such that the product flows from the transfer container 20 into the injection device 3.

A snap lock 8, 9 is provided between the adapter 2 and the storage container 1, such that the needle 6 is prevented from rotating in the septum 4.

Figure 3:
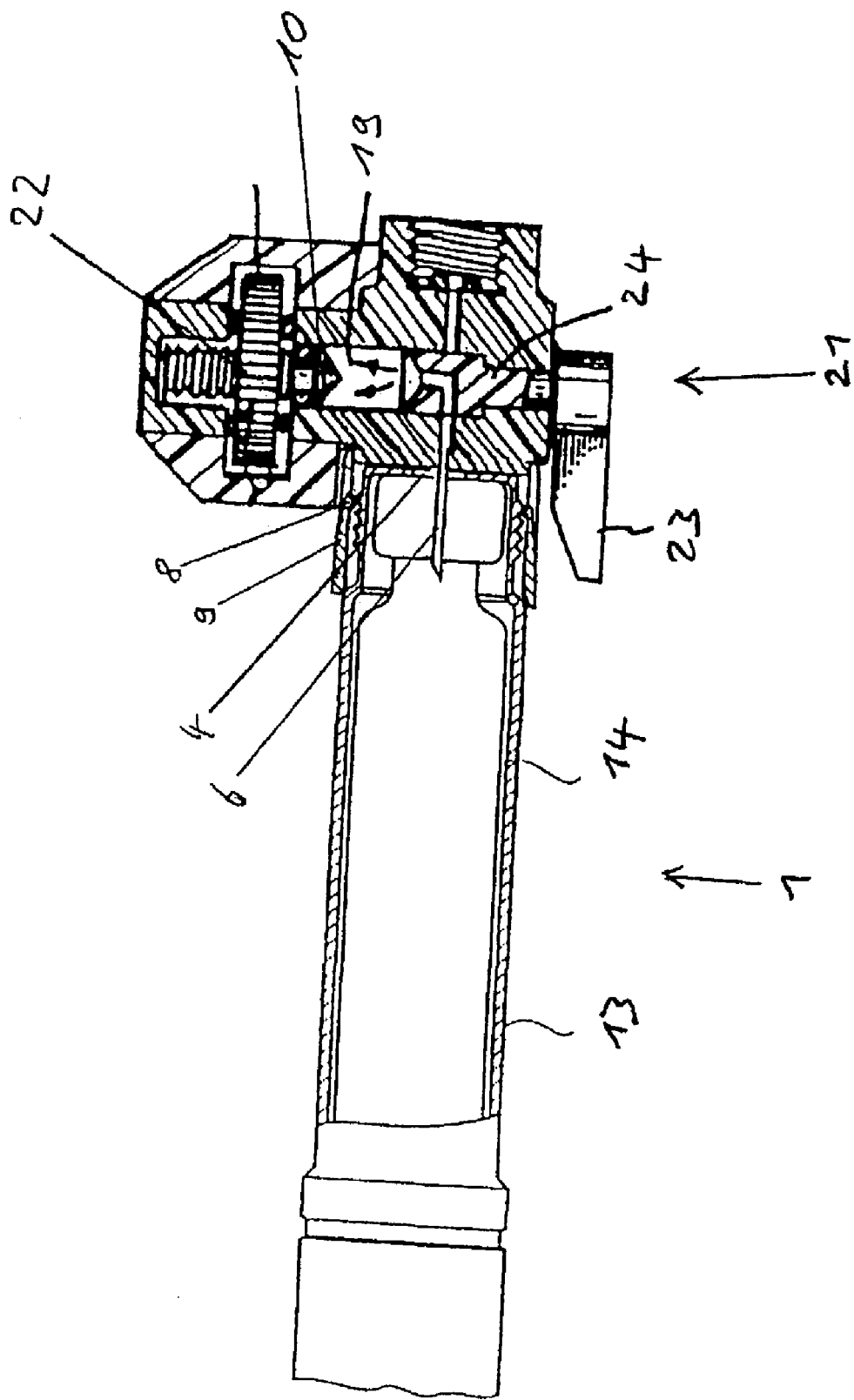
FIG. 3 depicts a storage container in combination with a transfer container comprising an integrated dosing means.

FIG. 3 shows a transfer container 21 comprising a duplex connector. A first connector of the transfer container 21 is provided for connecting to the storage container 1. A snap lock 8, 9 is provided, such that the needle 6 is prevented from rotating in the septum 4 and there is no rubber abrasion of the septum.

The second connector of the transfer container 21 is provided for connecting to a needleless injection device 3. A fluid gate 24 establishes a fluid connection either to the first connector or to the second connector. The fluid gate 24 is operated via a lever 23. Dosing using the transfer container 21 is performed analogously to dosing using the transfer container 20 described above. Once the product has been dosed into the transfer container 21, the fluid gate 24 is switched and a fluid connection is established between the transfer space 19 and the product space 18 of the injection device 3. The injection device 3 is filled by operating the dosing means 10, 22 in reverse.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A combination of a storage container for an injectable product and a needleless injection device for injecting the product, wherein an adapter is used to establish a fluid connection between the storage container and the injection device, and wherein the storage container is connected to a dosing means for dispensing the injectable product to the injection device in doses, and the dosing means includes an actuator operably coupled to the storage container, wherein the actuator is moveably disposed within the storage container.

2. The combination as set forth in claim 1, wherein the injection device comprises an injection opening.

3. The combination as set forth in claim 2, wherein the adapter comprises an opening which can be connected to the injection opening of the injection device.

4. The combination as set forth in claim 3, wherein the opening of the adapter and the injection opening are connected to each other by a seal.

5. The combination as set forth in claim 1, wherein the storage container is sealed by a membrane.

6. The combination as set forth in claim 5, wherein the adapter comprises a needle which penetrates the membrane of the storage container.

7. The combination as set forth in claim 5, wherein said membrane is a septum.

8. The combination as set forth in claim 1, wherein the storage container is a component of a device for administering the product in doses, to which device one of the adapter or an injection needle can be connected.

9. The combination as set forth in claim 8, wherein the connection is achieved by one of a snap lock or a screw lock.

10. The combination as set forth in claim 1, wherein the adapter is fixed to the storage container by means of a snap lock which can be snapped onto the storage container.

11. The combination as set forth in claim 1, wherein the adapter can be unscrewed from the storage container by turning.

12. The combination as set forth in claim 1, wherein the adapter can be removed from the storage container.

13. An injection device comprising:
    (a) an adapter component;
    (b) a storage container removeably coupled to the adapter component, the storage container configured to receive an injectable product;
    (c) an actuator moveably positioned within the storage container;
    (d) an injection component removeably coupled to the adapter component, the injection component configured to inject the injectable product, wherein the injection component and the storage container are in fluid communication through the adapter component; and
    (e) a dosing component configured to operate with the actuator to dispense the injectable product to the injection component in doses.

14. The injection device of claim 13 wherein the storage container is removeably coupled to the adapter component with a snap lock.

15. The injection device of claim 13 wherein the injection component is removeably coupled to the adapter component with a screw lock.

16. The injection device of claim 13 wherein the injection component is in fluid communication with the storage container through an opening in the injection component.

17. The injection device of claim 13 wherein the storage component is in fluid communication with the injection component through an opening in the storage container.

18. The injection device of claim 13 wherein the storage component is in fluid communication with the injection component through an opening in the adapter.

* * * * *